(12) United States Patent
Varlet et al.

(10) Patent No.: US 11,207,040 B2
(45) Date of Patent: Dec. 28, 2021

(54) DENTAL IMAGING APPARATUS WITH IMPROVED PATIENT POSITIONING

(71) Applicant: Trophy, Croissy-Beaubourg (FR)

(72) Inventors: Stephane Varlet, Croissy-Beaubourg (FR); Olivier Nesme, Croissy-Beaubourg (FR); Laurent Boutte, Croissy-Beaubourg (FR); Aude Lagardere, Croissy-Beaubourg (FR); Stephane Alric, Croissy-Beaubourg (FR)

( * ) Notice: Subject to any disclaimer, the term of this patent is extended or adjusted under 35 U.S.C. 154(b) by 0 days.

(21) Appl. No.: 16/472,632

(22) PCT Filed: Dec. 22, 2016

(86) PCT No.: PCT/IB2016/002002
§ 371 (c)(1),
(2) Date: Jun. 21, 2019

(87) PCT Pub. No.: WO2018/115923
PCT Pub. Date: Jun. 28, 2018

(65) Prior Publication Data
US 2019/0357861 A1    Nov. 28, 2019

(51) Int. Cl.
*A61B 6/14* (2006.01)
*A61B 6/00* (2006.01)

(52) U.S. Cl.
CPC .............. *A61B 6/14* (2013.01); *A61B 6/4435* (2013.01); *A61B 6/463* (2013.01); *A61B 6/466* (2013.01); *A61B 6/5223* (2013.01)

(58) Field of Classification Search
CPC . A61B 3/113; A61B 3/11; A61B 3/111; A61B 3/14; A61B 6/14; A61B 3/0008; A61B 3/0025; A61B 5/1121; A61B 5/1128; A61B 6/08; A61B 3/0041; A61B 3/0083; A61B 3/0091; A61B 3/024; A61B 3/028; A61B 3/032; A61B 3/103; A61B 3/145; A61B 5/0035; A61B 5/0088; A61B 6/032; A61B 6/03; A61B 6/4435; A61B 6/501; A61B 6/4441; A61B 6/461; A61B 5/0077; A61B 5/4542; A61B 6/4085; A61B 6/4417; A61B 6/488; A61B 6/54; A61B 5/1077; A61B 5/1079; A61B 6/463; A61B 6/466; A61B 6/5223; A61B 6/469; A61B 6/04; A61B 6/505; A61B 6/587; A61B 6/588;
(Continued)

(56) References Cited

U.S. PATENT DOCUMENTS

10,052,079 B2 * 8/2018 Abkai .................... A61B 6/547
2010/0217130 A1 * 8/2010 Weinlaender .......... A61B 1/247
600/476
(Continued)

*Primary Examiner* — Irakli Kiknadze (57) ABSTRACT

The invention concerns a dental imaging apparatus comprising: —a support frame, —a movable gantry that comprises two opposite arms respectively supporting an x-ray source and an x-ray sensor facing the x-ray source, —a movable patient positioning arm connected to the support frame, —two cameras positioned on the gantry arm supporting the x-ray source and on the positioning arm so as to respectively acquire side and front images of a patient's head, —a display assembly configured to simultaneously display in real time a side image and a front image of the patient's head taken by the two cameras.

15 Claims, 5 Drawing Sheets

(58) Field of Classification Search
CPC ............ A61B 6/589; A61B 2090/3937; A61B 6/0323; A61B 6/0492; A61B 6/52; A61B 6/5294; A61B 6/547; A61B 6/584; A61B 1/00101; A61B 1/00149; A61B 1/00174; A61B 1/04; A61B 1/247; A61B 6/4233; A61B 6/025; A61B 6/06; A61B 6/4452; A61B 6/5205; A61B 6/035; A61B 6/027; A61B 6/145; A61B 6/4464; A61B 6/467; A61B 8/0875; G06T 7/33; G06T 11/005; G06T 11/008; G06T 11/006; G06T 15/08; G06T 2211/436; G06T 15/20; G06T 2207/10081; G06T 2210/41; G06T 2211/432; G06T 7/0012; G06T 11/003; G06T 2207/10116; G06T 2207/30008; G06T 2207/30052; G06T 2211/40; G01D 11/245; A61C 19/04; H04N 19/142; H04N 19/172; H04N 19/50; H04L 67/1097; G01B 11/25; G01B 9/02004; G01B 9/0203; G01B 9/02091

USPC ............................................ 378/4, 38, 39, 62
See application file for complete search history.

(56) References Cited

U.S. PATENT DOCUMENTS

| | | | |
|---|---|---|---|
| 2011/0129058 A1* | 6/2011 | Ulrici | A61B 6/14 378/4 |
| 2015/0085080 A1* | 3/2015 | Hollenbeck | G01B 11/2545 348/47 |
| 2015/0156461 A1* | 6/2015 | Jessop | A61B 1/04 348/47 |
| 2016/0124249 A1* | 5/2016 | Haddadi | A61B 3/0041 351/204 |
| 2017/0311915 A1* | 11/2017 | Martino | A61B 6/501 |
| 2020/0085387 A1* | 3/2020 | Nyholm | A61B 6/469 |

* cited by examiner

DENTAL IMAGING APPARATUS WITH IMPROVED PATIENT POSITIONING

FIELD OF THE INVENTION

The invention relates generally to the field of extra-oral dental x-ray imaging.

BACKGROUND OF THE INVENTION

A conventional extra-oral dental x-ray imaging apparatus generally comprises:
a support frame,
a gantry that supports an x-ray source and an x-ray sensor in correspondence with the x-ray source and that is movable relative to the support frame,
a patient positioning arm that is connected to the support frame and movable relative thereto, the patient supporting arm being configured to position a head of a patient.

During an imaging process the patient is positioned between the x-ray source and the x-ray sensor. The x-ray source is energized so as to generate an x-ray beam which radiates the teeth of the patient before impinging the x-ray sensor. The gantry is driven into motion and follows a given path according to the imaging process.

The positioning of the patient's head is a key parameter for the quality of images acquired during the imaging process.

It would then be desirable to provide an improved or optimized position of the patient's head in view of a subsequent x-ray data acquisition or imaging process.

SUMMARY

It is an object of the present disclosure to advance the art of dental extra-oral imaging. Another object of this application is to address, in whole or in part, at least the foregoing and other deficiencies in the related art. It is another object of this application to provide, in whole or in part, at least the advantages described herein.

According to an aspect, a dental imaging apparatus for obtaining a radiographic image of a patient comprises:
a support frame,
a gantry that comprises two opposite arms respectively supporting an x-ray source and at least one x-ray sensor facing the x-ray source, the gantry being movable relative to the support frame,
a patient positioning arm that is connected to the support frame and movable relative thereto, the patient supporting arm being configured to position a head of a patient,
at least two cameras that are positioned so as to respectively acquire side and front images of the patient's head, a first camera being positioned on the gantry arm supporting the x-ray source and a second camera being positioned on the patient positioning arm,
a display assembly that is configured to simultaneously display in real time a side image and a front image of the patient's head taken by said first and second cameras.

Certain exemplary method and/or apparatus embodiments can provide simultaneous display of both side and front images of the patient's head, which provides great help in positioning the patient's head in view of a subsequent imaging process such as a 2D, a panoramic imaging process or a 3D imaging process. It is then quite easy and convenient to correct the position of the patient's head when simultaneously viewed on the display assembly.

According to other possible features:
the display assembly is further configured to display on each image at least one pattern that is superimposed on the patient's head, the at least one pattern being adapted to the setting of the apparatus in view of a subsequent x-ray data acquisition;
the apparatus is configured to cause the movement on each image of the at least one pattern relative to the patient's head until obtaining a position of said at least one pattern corresponding to a position of the head's patient relative to the apparatus that is adjusted as a function of the subsequent x-ray data acquisition;
the at least one pattern is selected among:
a plurality of anatomical landmarks in view of a subsequent panoramic x-ray data acquisition; and
a plurality of volumes of patient's head data to be acquired during a subsequent 3D x-ray data acquisition;
the at least one pattern that is displayed on the front image is the sagittal plane and the at least one pattern that is displayed on the side image is the Frankfurt plane or the Camper plane;
the display assembly is further configured to align the Frankfurt plane or the Camper plane of the patient's head on the side image with a horizontal position relative to a horizontal landmark displayed on the side image in response to an interaction of a user with the display assembly;
the apparatus is further configured to move the gantry and the patient positioning arm relative to the support frame in correspondence with the movement of the Frankfurt plane or the Camper plane of the patient's head on the side image;
the at least one pattern that is displayed on the side image is a projection in the plane of this image (Y, Z) of a volume of patient's head data to be acquired during a 3D x-ray data acquisition and the at least one pattern that is displayed on the front image is a vertical axis passing by a median part of this volume, the position of these two patterns on the respective side and front images providing the position of the volume of patient's head data that is to be acquired during a subsequent 3D x-ray data acquisition;
the apparatus is further configured to move the gantry relative to the support frame and the patient positioning arm and to cause the movement of the two patterns relative to the patient's head on their respective side and front images until obtaining a position corresponding to a position of the head's patient relative to the apparatus that is adjusted to the subsequent 3D x-ray data acquisition;
the display assembly is further configured to move one of the two patterns relative to the patient's head on the corresponding image in response to an interaction of a user on the display assembly until obtaining on display a position corresponding to a position of the head's patient relative to the apparatus that is adjusted to the subsequent 3D x-ray data acquisition, the apparatus being further configured to move accordingly the gantry relative to the support frame and the patient positioning arm.

Another aspect concerns a method for using a dental imaging apparatus for obtaining a radiographic image of a patient, the apparatus comprising:
a support frame,
a gantry that supports an x-ray source and at least one x-ray sensor facing the x-ray source, the gantry being movable relative to the support frame,
a patient positioning arm that is connected to the support frame and movable relative thereto, the patient supporting arm being configured to position the head of the patient, wherein the method comprises:
acquiring side and front images of the patient's head,
displaying in real time and simultaneously on a display assembly a side image and a front image of the patient's head
displaying on each image at least one pattern that is superimposed on the patient's head, the at least one pattern being adapted to the setting of the apparatus in view of a subsequent x-ray data acquisition.
According to other possible features:
the method further comprises moving the at least one pattern relative to the patient's head on each image until obtaining a position corresponding to a position of the head's patient relative to the apparatus that is adjusted as a function of the subsequent x-ray data acquisition;
the at least one pattern is selected among:
a plurality of anatomical landmarks in view of a subsequent panoramic x-ray data acquisition; and
a plurality of volumes or volume projections of patient's head data to be acquired during a subsequent 3D x-ray data acquisition;
the at least one pattern that is displayed on the front image is the sagittal plane and the at least one pattern that is displayed on the side image is the Frankfurt plane or the Camper plane;
the method comprises interacting with the display assembly to align the Frankfurt plane or the Camper plane of the patient's head on the side image with a horizontal position relative to a horizontal landmark displayed on the side image;
the method comprises beforehand interacting with the display assembly to define the Frankfurt plane or the Camper plane of the patient's head on the side image;
the method comprises beforehand displaying automatically the sagittal plane on the front image;
the method comprises changing the patient's head lateral orientation in view of the display of the sagittal plane superimposed on the patient's head on the front image;
the method comprises moving the gantry and the patient positioning arm relative to the support frame in correspondence with the movement of the Frankfurt plane or the Camper plane of the patient's head on the side image;
the at least one pattern that is displayed on the side image is a projection in the plane of this image (Y, Z) of a volume of patient's head data to be acquired during a 3D x-ray data acquisition and the at least one pattern that is displayed on the front image is a vertical axis, e.g., passing by a median part of this volume, the position of these two patterns on the respective side and front images provides the position of the volume of patient's head data that is to be acquired during a 3D x-ray data acquisition;
the method comprises moving the gantry relative to the support frame and the patient positioning arm, thereby causing the movement of the two patterns relative to the patient's head on their respective side and front images until obtaining a position corresponding to a position of the head's patient relative to the apparatus that is adjusted to the subsequent 3D x-ray data acquisition;
the method comprises interacting with the display assembly to move one of the two patterns relative to the patient's head on the corresponding image until obtaining on display a position corresponding to a position of the head's patient relative to the apparatus that is adjusted to the subsequent 3D x-ray data acquisition, thereby causing the gantry to be moved accordingly relative to the support frame and the patient positioning arm.

These objects are given only by way of illustrative example, and such objects may be exemplary of one or more embodiments of the invention. Other desirable objectives and advantages inherently achieved by the disclosed methods may occur or become apparent to those skilled in the art. The invention is defined by the appended claims.

BRIEF DESCRIPTION OF THE DRAWINGS

Other features and advantages will appear in the course of the remainder description, made by way of non-limiting examples, with reference to the following drawings:
FIG. 4b illustrates very schematically two simultaneously displayed side and front images in accordance with the method of FIG. 4a;
FIG. 5b illustrates very schematically two simultaneously displayed side and front images in accordance with the method of FIG. 5a.

DETAILED DESCRIPTION OF EXEMPLARY EMBODIMENTS

Figure 1:
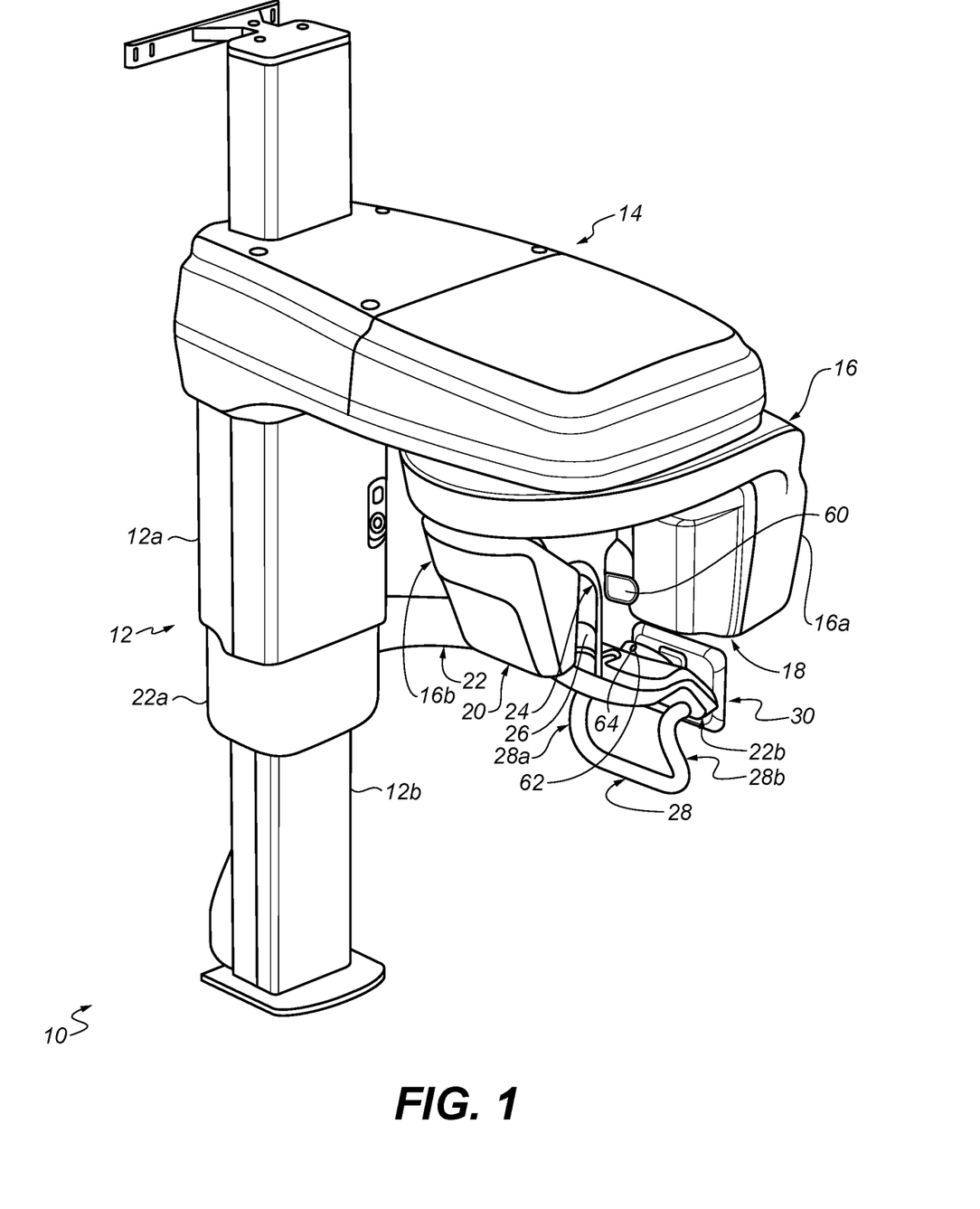
FIG. 1 depicts an overall schematic perspective view of an extra-oral imaging apparatus according to an embodiment of the invention.

FIG. 1 illustrates an embodiment of an extra-oral imaging apparatus 10. Apparatus 10 comprises a support structure that includes a support frame 12, which may be a support column.

The support structure also includes a horizontal mount 14 that may be supported or held by the vertical column 12. Horizontal mount 14 extends away from vertical column 12 and may be substantially perpendicular thereto. Horizontal mount 14 can move relative to the vertical column 12.

More particularly, horizontal mount 14 is fixedly mounted on a vertical part 12a that is slidably mounted over a fixed vertical part 12b. For example, an actuator, e.g. of the electric type, located behind the vertical column (not represented in the drawing) can be commanded to drive the horizontal mount 14 into a vertical movement in a controlled manner. Further explanation will be given in this respect subsequently.

Horizontal mount 14 can support a gantry 16. Gantry 16 is movable relative to the support structure, and more particularly to horizontal mount 14. Gantry 16 may more particularly be rotatable relative to horizontal mount 14. Gantry 16 may be rotatable about a vertical axis of rotation, which may be still during the operation of the imaging process or may follow one among several predetermined trajectories, in accordance with the selected imaging process. A known driving mechanism (not represented) for driving the gantry 16 into a given movement is integrated inside horizontal mount 14. By way of example, such driving mechanism includes motors for imparting a first movement in a X, Y plane, e.g. two step by step motors, and a motor for imparting a rotational movement about the vertical axis Z, e.g. a brushless motor.

Gantry 16 supports both an x-ray source 18 and at least one x-ray sensor 20 that is arranged in correspondence with the x-ray source. X-ray source 18 and the at least one x-ray sensor 20 may be arranged facing each other. Gantry 16 may include two opposite downwardly extending arms: a first arm 16a supports x-ray source 18 that is attached thereto and a second opposite arm 16b supports the at least one x-ray sensor 20 that is attached thereto.

When activated x-ray source 18 emits an x-ray beam that radiates all or part of an imaging area, e.g., a working area for placement of the patient's head before impinging the at least one x-ray sensor 20. In certain exemplary embodiments, an imaging area has a prescribed spatial relationship to the gantry 16 and/or the horizontal mount 14 (e.g., below or under).

In the present exemplary embodiment, the at least one x-ray sensor 20 may include a panoramic sensor, e.g. a slit-shaped sensor, a volumetric or computerized sensor (e.g. rectangular, square-shaped) or a cephalometric sensor or several sensors.

Depending on the sensor or sensors present in the apparatus, one or several operating modes or imaging processes (1, 2 or 3) may be used among the panoramic, volumetric or computerized tomography, and cephalometric modes.

The support structure may also include a patient positioning arm 22 that is connected to the support frame, and more particularly to the vertical column 12.

The patient positioning arm 22 is movable relative to the support frame. More particularly, arm 22 can slide along the vertical column 12 so as to move up or down upon command. The patient positioning arm 22 extends from an arm support 22a that is slidably mounted relative to the fixed vertical part 12b. For example, an actuator, e.g. of the electric type, located behind the vertical column (not represented in the drawing) can be commanded to drive the arm support 22a into a vertical movement in a controlled manner.

In the present embodiment, both the vertical part 12a and the arm support 22a can be moved as a single unit into a vertical movement along the fixed vertical part 12b.

Figure 2:
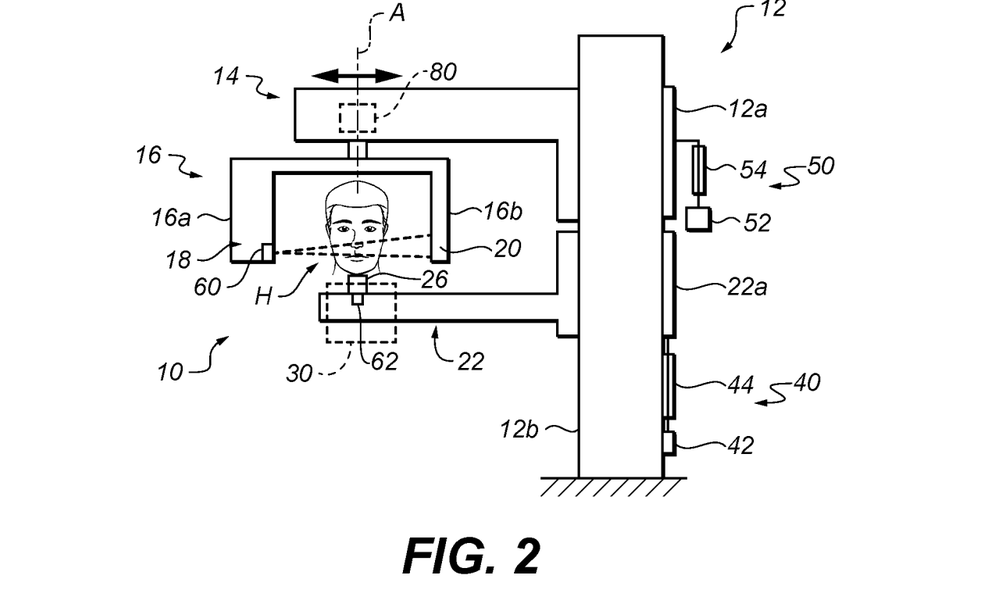
FIG. 2 is a very schematic side view of the apparatus of FIG. 1 illustrating functional units thereof.

FIG. 2 very schematically illustrates the possible mechanisms involved in the movements of the arm 22 and the horizontal mount 14. Only a head H of a patient has been represented.

In this respect, an actuator 40, e.g. of the electric type, located adjacent the vertical column can be commanded to drive in a controlled manner the set comprising the vertical part 12a and the arm support 22a into a vertical movement.

This vertical motion makes it possible to adjust the vertical position of the set relative to the height of the patient.

Actuator 40 comprises, e.g. a motor 42 and an endless screw 44 mounted at one of its two opposite ends on the output shaft of the motor, the other end being coupled to the above set.

Another actuator 50, e.g. of the electric type, located adjacent the vertical column can be commanded to drive in a controlled manner the vertical part 12a independently from the arm support 22a into a vertical movement.

This vertical motion makes it possible to adjust the height of the field of view generated by the x-ray imaging system (see the dotted line conical shape) relative to the patient's head.

Actuator 50 comprises, e.g. a motor 52 and an endless screw 54 mounted at one of its two opposite ends on the output shaft of the motor, the other end being coupled to the part 12a. For the sake of clarity actuator 50 has not been represented coupled to the fixed part of column 12 whereas it is coupled thereto.

Also, vertical rails (not represented on the drawing) are integrated on fixed part 12b and allow part 12a and arm support 22a to vertically slide relative to part 12b.

The patient positioning arm 22 extends along the apparatus in a direction that is substantially in correspondence with the direction of extension of horizontal mount 14 (FIGS. 1 and 2). Patient positioning arm 22 can be arranged sideways relative to the apparatus in a substantial parallel relationship with horizontal mount 14 (FIG. 2).

Patient positioning arm 22 serves to position the patient in the apparatus at a given location. In one embodiment, the patient positioning arm 22 can position the patient in the imaging area according to selection among operating modes of the apparatus 10.

Patient positioning arm 22 may include one or more patient positioning and/or holding systems generally located at a free end 22b of the arm or proximate thereto.

One or more patient positioning and/or holding systems allow to position the anatomical structures of the patient's head according to different orientations and to immobilize the patient's head during the examination so as to reduce any possible movement.

There exists one or several systems for each type of examination to be carried out. The arm 22 is configured to accommodate these systems.

As illustrated in FIG. 1, one of these systems, noted 24, includes two temporal holding members that extend upwardly from the arm 22 to which they are removably attached. Only one temporal holding member is represented, the other one being hidden by the arm 16b.

Another illustrated system is a chin support 26 that extends upwardly from the arm 22 to which it is removably attached. The chin support 26 is located between the two temporal holding members.

Other attachable, movable or integrated possible systems may be envisaged: a nasal support, a bite support etc.

A handle assembly 28 may be positioned at the free end 22b of the arm, underneath the arm and in a parallel relationship with the arm. This handle assembly 28 includes two vertical separate handle portions 28a, 28b which can be grasped by the patient when undergoing an imaging process so as to remain motionless.

Overall this handle assembly 28 has a U-shape which includes a horizontal base portion and two vertical upwardly-extending branches 28a, 28b that are fixed to the arm 22. Each branch plays the role of a vertical handle portion.

Patient positioning arm 22 also supports a monitor or display assembly 30 which makes it possible for a user of the apparatus to view and drive certain functions of the apparatus.

Apparatus 10 also includes at least two cameras that are positioned so as to respectively acquire side and front images of a patient's head.

In the present embodiment illustrated in FIG. 1, a first camera 60 is positioned on the gantry arm 16a supporting the x-ray source 18 and a second camera 62 is positioned on the patient positioning arm 22.

More particularly, first camera 60 may be positioned close to x-ray source 18, e.g. in an embedded manner, mounted on, or connected at, etc., but in a sideways position relative thereto, for example at an angle to the longitudinal direction of the x-ray beam generated by x-ray source 18. First camera 60 may be positioned at the same height (or different height) as x-ray source 18 relative to the arm 22 below. First camera 60 is configured to acquire side images of the patient's head.

FIG. 2 better illustrates the side position of camera 60 with respect to the patient's head H. In this FIG. the position of camera 60 is superimposed on the position of x-ray source 18.

More particularly, second camera 62 may be positioned in front of the patient's head and preferably under the head in a position situated at a low angle relative to the patient's head and to the x-ray source and sensor. In the present embodiment, second camera 62 may be embedded in, mounted on or connected at, etc. an appropriate housing or recess 64 provided on the arm 22.

FIG. 2 better illustrates an exemplary lowered front position of camera 62 with respect to head H.

Display assembly 30 (represented in dotted lines in FIG. 2) is configured to simultaneously display in real time a side image and a front image of the patient's head taken by first camera 60 and second camera 62 respectively. As the cameras are not positioned strictly perpendicularly to one side of the patient's head and in front of the patient's head respectively, before displaying images appropriate geometrical corrections are preferably applied to the images that are directly taken by the cameras based on the known geometry of the position of the cameras in the apparatus. Then the displayed images appear on the display assembly as though they were taken by correctly positioned cameras.

Figure 3:
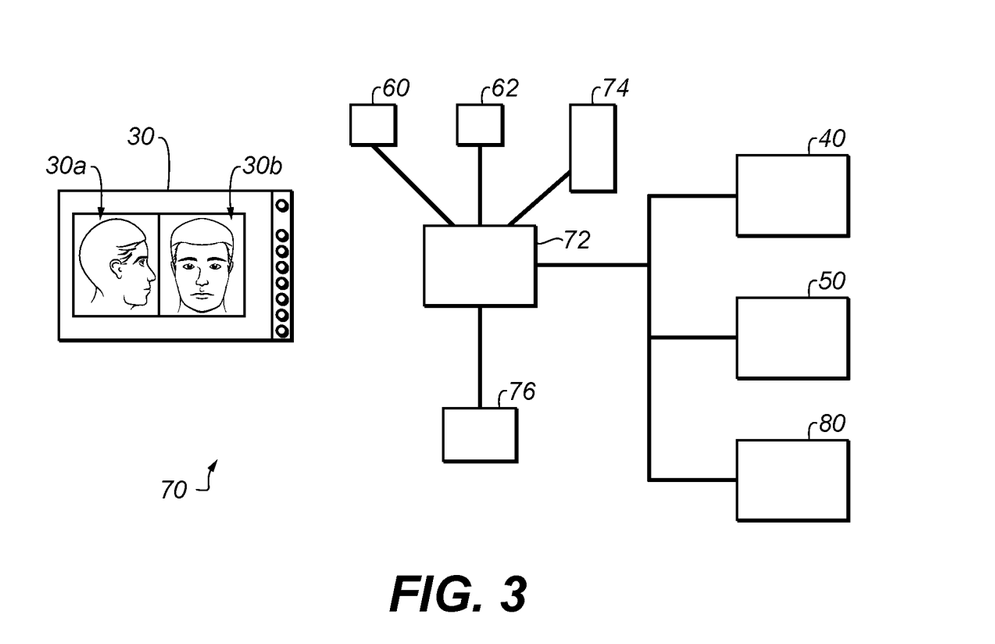
FIG. 3 is a schematic view of a functional system according to an embodiment of the invention.

FIG. 3 schematically depicts an overall functional system in the apparatus 10 according to one exemplary embodiment of the invention.

The system 70 of FIG. 3 may include:

the display assembly 30 comprising a single screen or two screens on which a side image 30a and a front image 30b of the patient's head H of FIG. 2 are represented; the screen may be a touch screen; the display assembly may also include control members 31 such as buttons, etc. that can be manually activated by a user;

a control assembly 72 connected to display assembly 30 and integrating in particular a processor; the processor is configured to carry out one or several computer programs stored inside control assembly 72 or elsewhere and that enable operation of the apparatus and its different components/units;

the first and second cameras 60 and 62 connected to the control assembly 72;

a storage element or unit 74 connected to the control assembly 72 and comprising, e.g. one or several electronic memories that can store some or all of the above-mentioned programs;

a manual control unit 76 that can be manually activated by a user and that is connected to the control assembly 72; this unit 76 can be coupled to the apparatus, e.g. to the arm 22 thereof, in one exemplary embodiment, the manual control unit can be physically controlled or remotely controlled, e.g., IR, voice, etc.;

actuators 40 and 50 already described above in connection with FIG. 2 and that are each connected to the control assembly 72.

The control assembly 72 can exchange data with the different units connected thereto. In particular, control assembly 72 can receive acquisition data from cameras 60, 62, commands entered through display assembly 30 and/or manual control unit 76 and it can send commands to actuators 40 and/or 50 to drive the motion of the corresponding units: the set comprising the vertical part 12a and the arm support 22a, on the one hand, and, the vertical part 12a, on the other hand. It is to be noted that the commands leading to the motion of these units may come either from display assembly 30 or manual control unit 76. Control assembly 72 can also send data as acquisition data to be stored to storage element 74.

One exemplary method for operating the apparatus according to an embodiment of the invention will now be described with reference to FIG. 4a that illustrates steps of the method under the form of an algorithm. This method is a method for providing a selected or an optimized patient positioning in view of a subsequent x-ray data acquisition or imaging process that is, here, a panoramic x-ray data acquisition or imaging process.

According to a first step S1 of the method, a patient is positioned under the gantry 16 with his/her head H positioned between x-ray source 18 and sensor 20 as illustrated in FIG. 2. The user adjusts at least one of the different patient positioning and/or holding systems described above. Alternatively or in addition, other patient positioning and/or holding systems may be used.

The user then selects an operating mode of the apparatus in view of the subsequent panoramic x-ray data acquisition (step S2). This selection may be manually carried out through appropriate display assembly control members 31 and start the implementation of the appropriate computer program or programs. In one exemplary embodiment, an operating mode can be automatically detected by the apparatus, e.g., a patient position, a sensor or the like.

In a further step S3, the cameras 60 and 62 are operated through unit 76 in cooperation with control assembly 72 so that each camera acquires image data corresponding to a side or profile view (camera 60) and a front view (camera 62).

Operation of the cameras may be performed by the user of the apparatus.

Alternatively, the cameras may be operated by the user through appropriate display assembly control members 31 in cooperation with control assembly 72.

According to another alternative, operation of the cameras may be performed automatically by the implementation of the dental imaging control program or programs.

Next (step S4), both images 30a and 30b are displayed simultaneously and in real time after appropriate prior geometrical correction has been applied, if desired.

Alternatively, the images may be displayed through an action from the user either through appropriate display assembly control members 31 or on the touch screen.

The user may display or cause to be displayed on each image at least one pattern that is superimposed on the patient's head (step S5). In one exemplary embodiment, the at least one pattern is an anatomical landmark that is adapted to the setting of the apparatus in view of the selected subsequent operating mode, panoramic x-ray data acquisition or imaging process. At least one anatomical landmark can be used as a guide to reach an optimized patient positioning.

In this respect, the at least one pattern that is displayed on the front image 30b is the sagittal plane and the at least one pattern that is displayed on the side image 30a is the Frankfurt plane or the Camper plane.

The sagittal plane is a vertical plane that divides the human body into right and left halves and that passes from anterior to posterior.

The Frankfurt plane contains a straight line passing through the ear canal and the bottom of the eye socket.

As an alternative, the Camper plane may be used. The Camper plane contains a straight line passing through the ear canal and the basis of the nose.

The user may display or cause to be displayed these patterns on the display assembly 30 according to different manners.

The user may touch the screen on the side image 30a and the front image 30b to locate a number of points that can respectively define the Frankfurt plane and the sagittal plane. The control assembly 72 then sends instructions to the display assembly 30 to draw a line connecting those points on each image.

The control assembly also commands the display of an horizontal line on the side image that will be used as a geometrical landmark for subsequent operation. To be noted that other geometrical landmarks than a horizontal line may be alternatively used.

Alternatively, the user may use a mouse (if the screen is not a touch screen) or another interacting device, e.g. an electronic pen, to touch the screen at various relevant locations.

Alternatively, an automatic process may be performed to automatically display the above patterns superimposed to the side and front images respectively through calculation algorithms based on appropriate image processing and automatic detection of relevant points defining the above-mentioned planes.

FIG. 4b is an enlarged view of the side and front images on display assembly 30 of FIG. 3.

As represented, the Frankfurt plane denoted FP and the horizontal line L1 are superimposed on the side image 30a and the sagittal plane SP illustrated by a vertical line is superimposed on the front image 30b.

The exemplary method further comprises a step S6 of interacting with the display assembly to align the Frankfurt plane FP of the patient's head (the same step may be applied to the Camper plane if the latter is selected) on the side image 30a with a horizontal position relative to the horizontal line L1 displayed on the side image. This alignment makes it possible to conveniently position the head in the antero-posterior direction in view of the subsequent panoramic x-ray data acquisition or imaging process. Alignment means here to make the Frankfurt plane FP parallel with the horizontal line L1 (e.g., a superimposition of both is not required).

In the side or lateral image displayed 30a, the head has a too high position and has to be bent down to adopt the correct position.

This correction can first be made on the display assembly by the user.

When the alignment of Frankfurt plane FP with horizontal line L1 has been achieved on display a signal is generated by the display assembly in cooperation with the control assembly to inform the user that the targeted position has been achieved. The signal may be visible on the screen (a change in the colour of Frankfurt plane FP and/or horizontal line), or audible, etc.

It is to be noted that while the patient moves the two cameras acquire video imaging data of the patient's head and recalculation in real time of the angular position of the two planes FP and SG is performed so that the displayed images always display these planes in the right position.

Once the targeted position has been achieved on the screen, it has to be transformed into a corresponding motion of the appropriate components/units of the apparatus.

Since the control assembly 72 precisely knows the range of movement on the screen of the coordinates of the Frankfurt plane FP, it can transform them into a corresponding range of movement of one or more functional unit(s) of the apparatus (step S7), in particular, here, the set comprising the part 12a (supporting the horizontal mount 14 and gantry 16) and arm support 22a (to which the patient positioning arm is coupled). Causing this functional unit of the apparatus to move correspondingly may be activated by the user, either through appropriate control members 31 on the display assembly or through manual control unit 76.

Alternatively, this movement can be automatically commanded by control assembly 72 once the targeted position on the screen has been achieved.

In the current situation, the whole set is commanded to move down through appropriate commands sent by control assembly 72 to actuator 40 of FIG. 2. In particular, this movement lowers the chin support 26, thereby allowing the head to bend down.

This movement is a mere non-limiting example and, of course, depending on the initial position of the head on the display assembly and the targeted position to reach, the movement of the set may be different, e.g. an upward movement.

It is to be noted that in another exemplary non-limiting configuration of the apparatus where the patient positioning arm can be moved independently from the horizontal mount and associated gantry, the patient positioning arm could be commanded to move to correct the head's position in register with the motion on the screen without moving the gantry.

The sagittal plane SG displayed on the front image 30b is preferably automatically centered on the nose of the patient's head and in a vertical position. If the head makes a tilt to the vertical axis, then the user may correct the position of the head, generally manually and check the targeted position on the screen. Alternatively, a head positioning assembly can be used.

In one exemplary embodiment, a vertical pattern (e.g., a vertical line) is in the middle of ht image and is fixed, tobe superimposed on the patient's face. In this case, the patient head can be positioned (e.g., manually or remotely automated) such that the vertical line matches the selected vertical orientation such as the sagittal plane of the patient (e.g., passes along the nasal bone, through the middle of the eyes middle fo the chin, etc.).

In the correct position, the head is preferably or must not be tilted to the right or to the left. This step may be performed during step S6, after the latter or even after step S7 has been achieved.

The method ends at step S8.

Figure 4A:
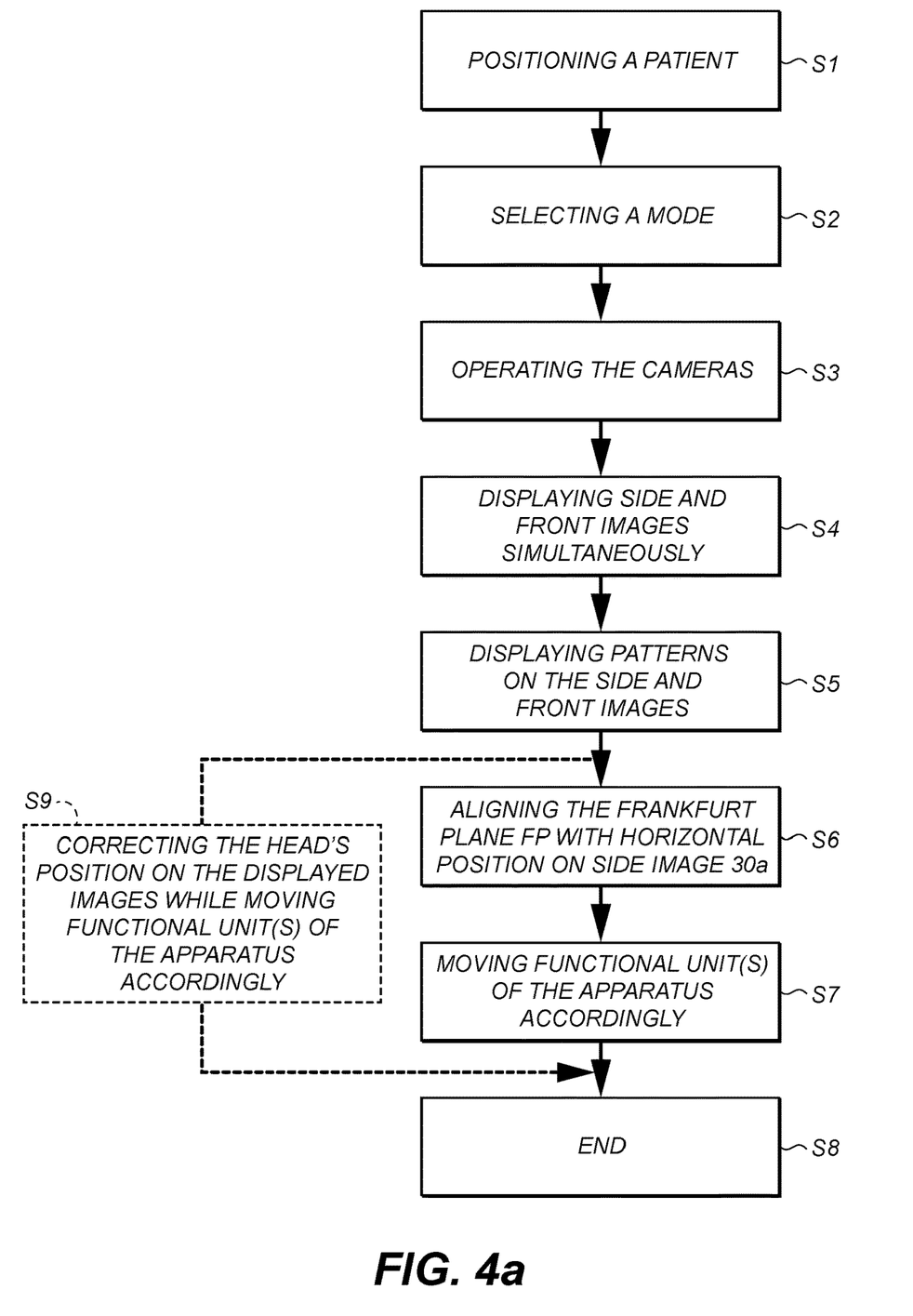
FIG. 4a is an algorithm representing a method according to an embodiment of the invention.
Figure 4B:
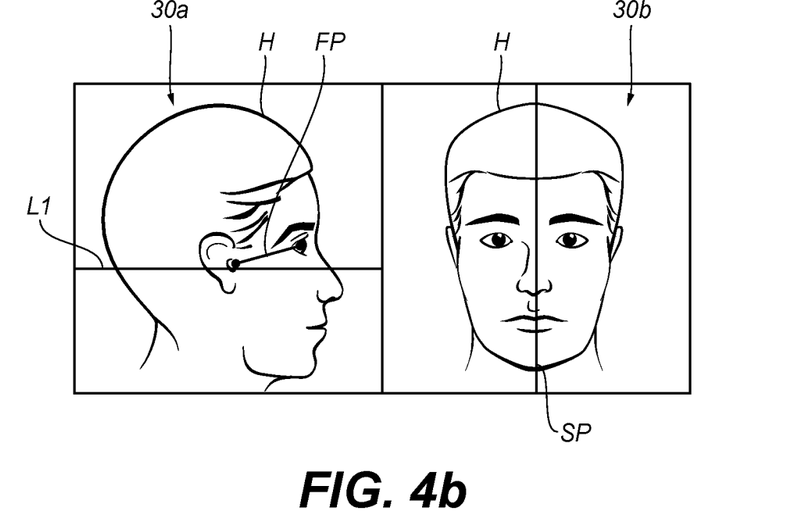

An exemplary variant embodiment of the method is illustrated in dotted lines on FIG. 4a.

According to this variant, steps S6 and S7 are performed simultaneously in the course of step S9 instead of being performed sequentially: the movements of the Frankfurt plane FP on the screen are simultaneously converted into corresponding movement(s) of the above functional units as described above.

This can be automatically performed by control assembly 72 in conjunction with display assembly while Frankfurt plane FP is moved on the screen to achieve a parallel relationship with horizontal line L1.

According to another exemplary variant embodiment, the corresponding movement(s) of the functional units may take place in a time-delayed manner but not sequentially as in steps S6 and S7.

A method for operating the apparatus according to another exemplary embodiment of the invention will now be described with reference to FIG. 5a that illustrates steps of the method under the form of an algorithm. This method is a method for providing a selected or an optimized patient positioning in view of a subsequent x-ray data acquisition or imaging process that is, here, a 3D x-ray data acquisition or imaging process.

According to a first step S10 of the method, a patient is positioned under the gantry 16 with his/her head H positioned between x-ray source 18 and sensor 20 as illustrated in FIG. 2. The user adjusts at least one of the different patient positioning and/or holding systems described above. Alternatively or in addition, other patient positioning and/or holding systems may be used.

The user then selects an operating mode of the apparatus in view of the subsequent 3D x-ray data acquisition (step S11). This selection may be manually carried out through appropriate display assembly control members 31 and start the implementation of the appropriate computer program or programs.

In a further step S12, the cameras 60 and 62 are operated through unit 76 in cooperation with control assembly 72 so that each camera acquires image data corresponding to a side or profile view (camera 60) and a front view (camera 62).

Operation of the cameras may be performed by the user of the apparatus.

Alternatively, the cameras may be operated by the user through appropriate display assembly control members 31 in cooperation with control assembly 72.

According to another alternative, operation of the cameras may be performed automatically by the implementation of the program or programs.

Next (step S13), a side image 60a and a front image 60b are displayed simultaneously and in real time after appropriate prior geometrical corrections have been applied. FIG. 5b is an enlarged view of the side and front images on display assembly 30 of FIG. 3.

Alternatively, the images may be displayed through an action from the user either through appropriate display assembly control members 31 or on the touch screen.

The user may display or cause to be displayed on each image at least one pattern (e.g., volume and positioning of the volume) that is superimposed on the patient's head (step S14). In the present exemplary embodiment, the at least one pattern is adapted to the setting of the apparatus in view of the selected subsequent 3D x-ray data acquisition or imaging process. The at least one pattern will be used as a guide to reach a selected or an optimized patient positioning.

In the present exemplary embodiment, the at least one pattern that is displayed on the side image 60a represents a volume of patient's head data to be acquired during a subsequent 3D x-ray data acquisition. The volume V that is displayed simulates the Field Of View (FOV) to be acquired and its position relative to the profile of the head H.

To be more precise, the at least one pattern that is displayed on the side image 60a is a projection in the plane of this image (Y, Z) of a volume of patient's head data to be acquired during a 3D x-ray data acquisition.

The at least one pattern that is displayed on the front image 60b is a vertical axis L2 passing by a median part of the volume V (the projection of which is displayed on side image 60a) and that simulates the lateral position of the volume on either lateral part of the sagittal plane. It is to be understood that appropriate calculation algorithms implemented by control assembly 72 make it possible to link the side and front images so that a movement imparted to the volume projection on side image 60a, e.g. a movement from the anterior to the posterior position (i.e. from left to right) or the reverse or an upward or downward movement, automatically causes a corresponding lateral movement of the axis L2 on front image 60b and the reverse.

Practically, the user may display or cause to be displayed a volume (i.e. here, its projection on the plane of side image 60a) on side image 60a, e.g. through appropriate display assembly control members 31, with a finger on the touch screen, or with a mouse, a pen or another similar device interacting with the screen. The user does not select the location of the displayed volume projection V on the patient's face. The location of the displayed volume projection is defined by default by the control assembly together with the display assembly. Also, the volume projection V is displayed with a displayed size that is defined by default. The axis L2 is automatically displayed on the front image 60b since the two images are linked as explained above.

The volume V is selected by the user among several predetermined volumes, e.g. ranging from 5×5 cm to 10×10 cm. The selection step S15 may be performed before step S14 or at the same time. This selection step S15 may be performed manually by the user, e.g. through appropriate display assembly control members 31 or on the touch screen. Once the selected volume has been validated by the user the volume projection V is displayed with the selected volume size. The selection step S15 can be optional.

In the present exemplary embodiment, each volume is typically a cylindrical volume and the volume projection may be a square or a rectangle.

Next (step S16), the user may move the displayed volume projection V on the side image 60a to reach a targeted position, i.e. a selected zone of the patient's face. Once the selected zone has been validated by the user it remains displayed in this selected position. As a variant, the user may alternatively move the displayed axis L2 on front image 60b. Step S16 may be performed by the user, e.g. through appropriate display assembly control members 31, with a finger on the touch screen, or with a mouse, a pen or another similar device interacting with the screen. An example of a possible movement has been illustrated on side image 60a through an arrow and a dotted line targeted zone. The corresponding movement of axis L2 on the front image has also been illustrated by an arrow and a shifted vertical position of axis L2 in dotted lines.

Alternatively, the user may select a targeted zone of the patient's face on the side image 60a, e.g. through appropriate display assembly control members 31, with a finger on the touch screen, or with a pen or another similar device interacting with the screen. Once the selected zone has been validated by the user, e.g. through appropriate display assembly control members 31, a projection of volume V is automatically displayed on the selected zone (via the control assembly together with display assembly) with a displayed size that is defined by default. The same description as above also applies for the selection of a size.

The position of these two patterns on the respective side and front images provides the adjusted/targeted position of the volume of patient's head data that will be acquired during the subsequent 3D x-ray data acquisition.

Once the targeted position has been achieved on the screen, it has to be transformed into a corresponding motion of the appropriate components/units of the apparatus.

Since the control assembly 72 precisely knows the range of movement on the screen of the coordinates of volume projection V, it can transform them into a corresponding range of movement of one or more functional unit(s) of the apparatus (step S17). Here, the gantry 16 preferably has to be moved relative to the patient positioning arm 22 that stays motionless so as to adjust the height of the gantry relative to the patient's head. This will make it possible to adjust the position of the x-ray source and associated sensor to the patient's head and, therefore, the volume projection V that will be generated and directed towards the selected zone of the patient's head in the course of the subsequent 3D imaging process. Also, an appropriate movement of the gantry 16 relative to horizontal mount 14, i.e. in a horizontal plane (X, Y coordinates), is commanded by control assembly 72 to move the axis of rotation of the gantry perpendicularly to the horizontal plane. Appropriate commands are generated by control assembly 72 and sent to at least one actuator 80 (see FIGS. 2 and 3) so as to command the lateral displacement of the gantry axis A as represented by the double arrow in FIG. 2. Actuator 80 may be located in horizontal mount 14 (dotted lines in FIG. 2) and comprise the above-described motors for impairing a X, Y displacement of the axis A.

Thus, the part 12a (supporting the horizontal mount 14 and gantry 16) may be moved upwardly or downwardly relative to arm support 22a (to which the patient positioning arm 22 is coupled).

Causing this functional unit of the apparatus to move correspondingly may be activated by the user, either through appropriate control members 31 on the display assembly or through manual control unit 76.

In response to the above user input commands appropriate commands are generated and sent by control assembly 72 to actuator 50 of FIG. 2 in order to raise or lower part 12a accordingly and to actuator 80 to horizontally/laterally shift the axis of rotation of the gantry.

Alternatively, this movement can be automatically commanded by control assembly 72 once the targeted position on the screen has been achieved without any other user input commands.

The method ends at step S18.

Figure 5A:
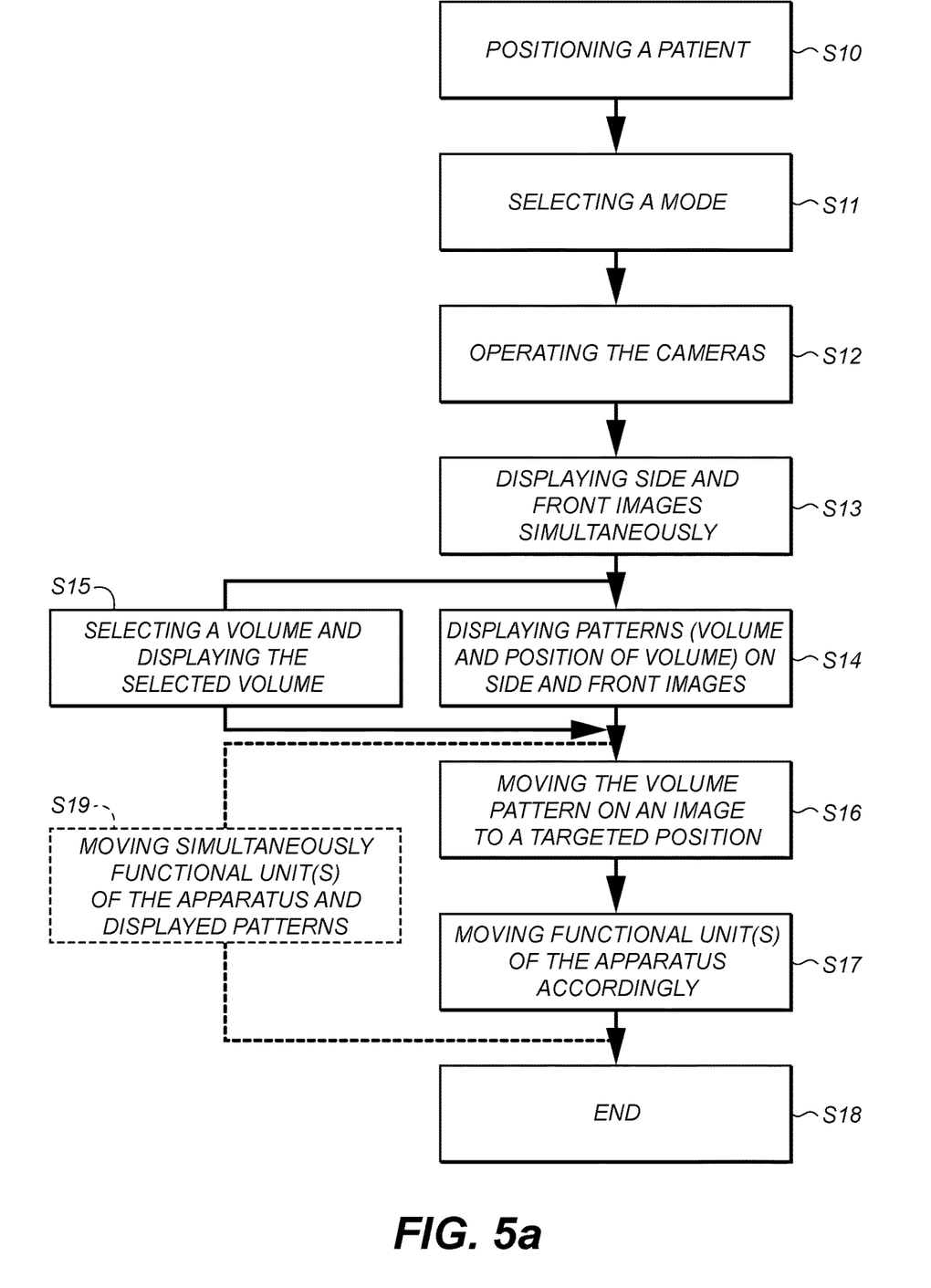
FIG. 5a is an algorithm representing a method according to an embodiment of the invention.
Figure 5B:
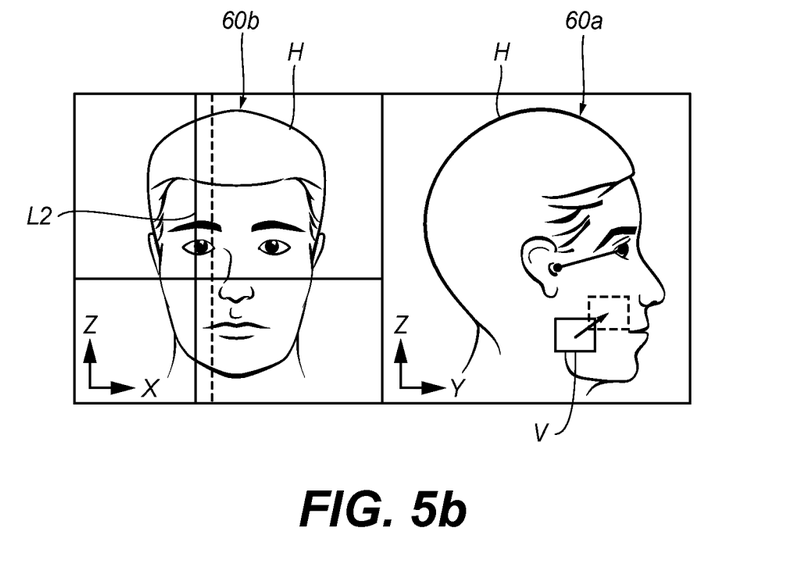

An exemplary variant embodiment of the method illustrated in dotted lines on FIG. 5a.

According to this variant steps S16 and S17 are performed simultaneously in the course of step S19: the movements of one of the above patterns (volume projection V and axis L2) on the screen are simultaneously converted into corresponding movements of the above functional units as described above. For example, when a user moves the volume position (e.g., square position) on the side view 30a, the position of the volume in can be directly adjusted in Y,Z orientations for a dental imaging apparatus like apparatus 10. Further, when a user moves the additional vertical line on the front view 30b, the position of the volume can be adjusted in the X orientation. Each modification in X,Y,Z on the side view 30a and the front view 30b (e.g., square, additional vertical line) will induce an immediate modification of the gantry position to set a correct patient position and/or enabling an accurate volume acquisition in the desired location. This can be automatically performed by control assembly 72 in conjunction with the display assembly 30 while one of these patterns is moved on the screen to achieve a targeted position.

According to another exemplary variant embodiment, the corresponding movement(s) of the functional units are firstly commanded by the user, e.g. through appropriate control members 31 on the display assembly or through manual control unit 76, and the displayed patterns on the screen are caused to move accordingly through the action of control assembly 72 together with display assembly 30.

According to still another exemplary variant embodiment, the corresponding movement(s) of the functional units may take place in a time-delayed manner but not sequentially as in steps S16 and S17.

Whatever the embodiment described above, when the set (part 12a and support arm 22a) or only part 12a is moved, it is to be noted that the embedded cameras also move.

In some of the above embodiments the patterns displayed on the side and front images may be moved (at least one pattern may be moved) on the corresponding image in accordance with one or several movements of one or more functional units of the apparatus or the movement of the displayed pattern or patterns may cause one or several corresponding movements of one or more functional units of the apparatus.

The above-described apparatus and/or methods are very helpful to get a desired or an optimized position of the patient's head that will be used in a subsequent x-ray data acquisition or imaging process. The above-described methods and/or apparatus make it possible to easily, reliably and quickly optimize this position. Exemplary positions of the patient's head can define settings of the apparatus (in particular of its functional unit or units) that have to be achieved in order to optimally perform the corresponding subsequent x-ray data acquisition or imaging process.

Although the above has been described in relation with a panoramic and 3D imaging process (e.g. of the CBCT type, i.e. Cone Beam Computerized Tomography type), other imaging processes such as a cephalometric imaging process.

In one exemplary embodiment, an examination can be a 2D image acquisition. In this case, a user can interacting with only a side image (e.g., 30a) and use the display to select at least two anatomical land marks (inferior margin of orbit bone and ear canal) to define a line segment, which when visually shown to the user can be used to move (e.g., up, down) a patient positioning apparatus (e.g., arm 22) such as the chin support to orient the patient head to get the line in the desired orientation or horizontal. Thus, with only a side or lateral image displayed 30a, the head can be maneuvered to adopt the correct position for a 2D x-ray image use. Once oriented, In one embodiment, that orientation can be transformed into a corresponding motion of the appropriate components/units of the apparatus.

In one exemplary embodiment, the real time display of the side image 30a and the front image 30b is achieved through sequential display on a single viewing surface. Preferably, the side image 30a and the front image 30b are displayed for a prescribed time each, which can be the same or different. Alternatively, the side image 30a and the front image 30b can be manually alternated in accordance with specific actions by the user.

Other possible patient positioning embodiments may be envisaged within the scope of the invention. In one exemplary embodiment, a 3D semi-transparent cylindrical volume can be shown in side and front views generated by the cameras 60, 62 or in a 3D volume of the patient head, which is oriented in the display assembly 30 by the cameras 60, 62.

Certain exemplary method and/or apparatus embodiments according to the application can provide real time display (e.g., simultaneous) of both side and front images of the patient's head, which allows accurate and/or repeatable positioning of a patient (e.g., dentition) in view of a subsequent imaging process such as a 2D, a panoramic imaging process or a 3D imaging process. It is then quite easy and/or convenient to correct the position of the patient when simultaneously viewed (e.g., on a display). Further, positioning of a dental x-ray acquisition gantry can be controlled by the simultaneous display of both side and front images of the patient's head.

Exemplary embodiments according to the application can include various features described herein (individually or in combination). Although embodiments of the present disclosure are illustrated using dental imaging apparatus, similar principles can be applied for other types of diagnostic imaging and for other anatomy.

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations/embodiments, such feature can be combined with one or more other features of the other implementations/embodiments as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by at least the following claims.

The invention claimed is:

1. A dental imaging apparatus for obtaining a radiographic image of a patient, the apparatus comprising:
   a support frame,
   a gantry that comprises two opposite arms respectively supporting an x-ray source and at least one x-ray sensor facing the x-ray source, the gantry being movable relative to the support frame,
   a patient positioning arm that is connected to the support frame and movable relative thereto, the patient supporting arm being configured to position a head of a patient,
   at least two cameras that are positioned so as to respectively acquire side and front images of the patient's head, a first camera being positioned on the gantry arm supporting the x-ray source and a second camera being positioned on the patient positioning arm,
   a display assembly that is configured to simultaneously display in real time a side image and a front image of the patient's head taken by said first and second cameras.

2. The dental imaging apparatus of claim 1, wherein the display assembly is further configured to display on each image at least one pattern that is superimposed on the patient's head, the at least one pattern being configured to the setting of the apparatus in view of a subsequent x-ray data acquisition.

3. The dental imaging apparatus of claim 2, wherein the at least one pattern is selected among:
   a plurality of anatomical landmarks in view of a subsequent panoramic x-ray data acquisition; and
   a plurality of volumes or volume projections of patient's head data to be acquired during a subsequent 3D x-ray data acquisition.

4. The dental imaging apparatus of claim 3, wherein the at least one pattern that is displayed on the front image is the sagittal plane and the at least one pattern that is displayed on the side image is the Frankfurt plane or the Camper plane.

5. The dental imaging apparatus of claim 4, wherein the display assembly is further configured to align the Frankfurt plane or the Camper plane of the patient's head on the side image with a horizontal position relative to a horizontal landmark displayed on the side image in response to an interaction of a user with the display assembly.

6. The dental imaging apparatus of claim 5, wherein the apparatus is further configured to move the gantry and the patient positioning arm relative to the support frame in correspondence with the movement of the Frankfurt plane or the Camper plane of the patient's head on the side image.

7. The dental imaging apparatus of claim 3, wherein the at least one pattern that is displayed on the side image is a projection in the plane of this image (Y, Z) of a volume of patient's head data to be acquired during a 3D x-ray data acquisition and the at least one pattern that is displayed on the front image is a vertical axis passing by a median part of this volume, the position of these two patterns on the respective side and front images providing the position of the volume of patient's head data that is to be acquired during a subsequent 3D x-ray data acquisition.

8. The dental imaging apparatus of claim 7, wherein the apparatus is further configured to move the gantry relative to the support frame and the patient positioning arm and to cause the movement of the two patterns relative to the patient's head on their respective side and front images until obtaining a position corresponding to a position of the head's patient relative to the apparatus that is adjusted to the subsequent 3D x-ray data acquisition.

9. A method for using a dental imaging apparatus for obtaining a radiographic image of a patient, the apparatus comprising:
   a support frame,
   a gantry that supports an x-ray source and at least one x-ray sensor facing the x-ray source, the gantry being movable relative to the support frame,
   a patient positioning arm that is connected to the support frame and movable relative thereto, the patient supporting arm being configured to position the head of the patient,
   wherein the method comprises:
   acquiring side and front images of the patient's head,
   displaying in real time and simultaneously on a display assembly a side image and a front image of the patient's head,
   displaying on each image at least one pattern that is superimposed on the patient's head, the at least one pattern being configured to the setting of the apparatus in view of a subsequent x-ray data acquisition.

10. The method of claim 9, wherein the at least one pattern is selected among:
    a plurality of anatomical landmarks in view of a subsequent panoramic x-ray data acquisition; and
    a plurality of volumes or volume projections of patient's head data to be acquired during a subsequent 3D x-ray data acquisition.

11. The method of claim 10, wherein the at least one pattern that is displayed on the front image is the sagittal plane and the at least one pattern that is displayed on the side image is the Frankfurt plane or the Camper plane.

12. The method of claim 11, wherein the method comprises interacting with the display assembly to align the Frankfurt plane or the Camper plane of the patient's head on the side image with a horizontal position relative to a horizontal landmark displayed on the side image.

13. The method of claim 11, wherein the method comprises moving the gantry and the patient positioning arm relative to the support frame in correspondence with the movement of the Frankfurt plane or the Camper plane of the patient's head on the side image.

14. The method of claim 10, wherein the at least one pattern that is displayed on the side image is a projection in the plane of this image (Y, Z) of a volume of patient's head data to be acquired during a 3D x-ray data acquisition and the at least one pattern that is displayed on the front image is a vertical axis passing by a median part of this volume, the position of these two patterns on the respective side and front images providing the position of the volume of patient's head data that is to be acquired during a 3D x-ray data acquisition.

15. The method of claim 14, wherein the method comprises moving the gantry relative to the support frame and the patient positioning arm, thereby causing the movement of the two patterns relative to the patient's head on their respective side and front images until obtaining a position corresponding to a position of the head's patient relative to the apparatus that is adjusted to the subsequent 3D x-ray data acquisition.

* * * * *